United States Patent [19]
Prosser et al.

[11] Patent Number: 5,209,123
[45] Date of Patent: May 11, 1993

[54] METHODS OF DETERMINING LOADS AND FIBER ORIENTATIONS IN ANISOTROPIC NON-CRYSTALLINE MATERIALS USING ENERGY FLUX DEVIATION

[75] Inventors: William H. Prosser, Newport News; Ronald D. Kriz, Blacksburg, both of Va.; Dale W. Fitting, Golden, Colo.

[73] Assignee: The United States of America as represented by the Administrator of the National Aeronautics and Space Administration, Washington, D.C.

[21] Appl. No.: 797,507

[22] Filed: Nov. 22, 1991

[51] Int. Cl.$^5$ .................................................. G01N 3/00
[52] U.S. Cl. ........................................... 73/788; 73/641
[58] Field of Search .................. 73/862.59, 778, 641, 73/599, 643, 633, 596, 788

[56] References Cited

U.S. PATENT DOCUMENTS

| 3,995,501 | 12/1976 | Wiley | 73/597 |
| 4,033,182 | 7/1977 | Clotfelter | 73/597 |
| 4,080,836 | 3/1978 | Thompson et al. | 73/597 |
| 4,457,174 | 7/1984 | Bar-Cohen et al. | 73/633 |
| 4,499,770 | 2/1985 | Kriz | 73/599 |
| 4,754,645 | 7/1988 | Piche et al. | 73/597 |
| 4,856,335 | 8/1989 | Tornberg | 73/597 |

OTHER PUBLICATIONS

Williams, J. H. and Doll, B., "Ultrasonic Attenuation as an Indicator of Fatigue Life of Graphite Fiber Epoxy Composite", Sep. 1979.
Wu et al, "Harmonic generation measurements in unidirectional graphite/epoxy composite", Rev. of Progress in Quantitative Nondestructive Eval. vol. 108, Ed. D. O. Thompson and D. E. Chimenti, Plenum Press (1991), pp. 1476-1477.
W. H. Prosser, "Ultrasonic characterization of the non-linear elastic properties of unidirectional graphite/epoxy composites", NASA Contractor Report 4100, Oct. 1987.

Primary Examiner—Hezron E. Williams
Assistant Examiner—Nashmiya Ashraf
Attorney, Agent, or Firm—Kevin B. Osborne

[57] ABSTRACT

An ultrasonic wave is applied to an anisotropic sample material in an initial direction and an angle of flux deviation of the ultrasonic wave front is measured from this initial direction. This flux deviation angle is induced by the unknown applied load. The flux shift is determined between this flux deviation angle and a previously determined angle of flux deviation of an ultrasonic wave applied to a similar anisotropic reference material under an initial known load condition. This determined flux shift is then compared to a plurality of flux shifts of a similarly tested, similar anisotropic reference material under a plurality of respective, known load conditions, whereby the load applied to the particular anisotropic sample material is determined. A related method is disclosed for determining the fiber orientation from known loads and a determined flux shift.

14 Claims, 3 Drawing Sheets

METHODS OF DETERMINING LOADS AND FIBER ORIENTATIONS IN ANISOTROPIC NON-CRYSTALLINE MATERIALS USING ENERGY FLUX DEVIATION

ORIGIN OF THE INVENTION

The invention described herein was made by employees of the United States Government and may be manufactured and used by or for the Government for governmental purposes without the payment of any royalties thereon or therefor.

BACKGROUND OF THE INVENTION

1. Technical Field of the Invention

The present invention relates generally to load monitoring and more particularly to a method of determining loads and fiber orientations in anisotropic materials using energy flux deviation.

2. Discussion of the Related Art

In isotropic materials, the direction of the energy flux (energy per unit time per unit area) of an ultrasonic plane wave is always along the same direction as the normal to the wave front. In anisotropic materials, however, this is true only along symmetry directions. Along other directions, the energy flux of the wave deviates from the intended direction of propagation. This phenomenon is known as energy flux deviation and is illustrated in FIG. 1. An ultrasonic transducer U is coupled to an anisotropic crystalline material AM and directs an ultrasonic wave through the material as indicated by directional arrow N which is normal to the wave front. The anisotropic nature of the material causes the energy flux to deviate from the normal arrow N by an energy flux deviation angle A, resulting in an energy flux vector V associated with the deviated wave flow W. The direction of the energy flux is dependent on the elastic coefficients of the material. This effect has been demonstrated in many anisotropic crystalline materials. In transparent quartz crystals, Schlieren photographs have been obtained which allow visualization of the ultrasonic waves and the energy flux deviation.

The energy flux deviation in graphite/epoxy (gr/ep) composite materials can be quite large because of their high anisotropy. The flux deviation angle has been calculated for unidirectional gr/ep composites as a function of both fiber orientation and fiber volume content. Experimental measurements have also been made in unidirectional composites. It has been further demonstrated that changes in composite materials which alter the elastic properties such as moisture absorption by the matrix or fiber degradation can be detected nondestructively by measurements of the energy flux shift.

Graphite fiber-reinforced composites such as graphite/epoxy, graphite/magnesium and graphite/aluminum exhibit very high stiffness-to-weight and strength-to-weight ratios, making them excellent materials for lightweight aerospace structures. Since these structures are intended primarily to carry load, the in-situ and non-destructive determination of load and load induced quantities such as stress is very desirable. The energy flux of stress waves, i.e., waves affected by a load, propagating through anisotropic crystals has been shown to deviate from the direction of the normal to the plane wave. However, there has been no known indication that this deviation can be correlated with the amount of applied load. This lack of knowledge is not surprising since crystals are normally not used in load bearing applications. In addition, there is no known work concerning any energy flux deviation in highly anisotropic, non-crystalline materials such as graphite fiber-reinforced composites and consequently no known work concerning any effect of applied load on such deviations.

OBJECTS

It is accordingly an object of the present invention to determine load and load induced quantities such as stress and strain in anisotropic materials using energy flux deviations.

It is another object of the present invention to accomplish the foregoing object non-destructively.

It is a further object of the present invention to accomplish the foregoing objects in a simple manner.

Additional objects and advantages of the present invention are apparent from the specification and drawings which follow.

SUMMARY OF THE INVENTION

The foregoing and additional objects are obtained by a method of determining a load applied to a particular anisotropic sample material according to the present invention. An ultrasonic wave is applied to the anisotropic sample material in an initial direction and an angle of flux deviation of the ultrasonic wave front is measured from this initial direction. This flux deviation angle is induced by the unknown applied load. The flux shift is determined between this flux deviation angle and a previously determined angle of flux deviation of an ultrasonic wave applied to a similar anisotropic reference material under an initial known load condition. This determined flux shift is then compared to a plurality of flux shifts of a similarly tested, similar anisotropic reference material under a plurality of respective, known load conditions, whereby the load applied to the particular anisotropic sample material is determined.

DETAILED DESCRIPTION

Figure 1:
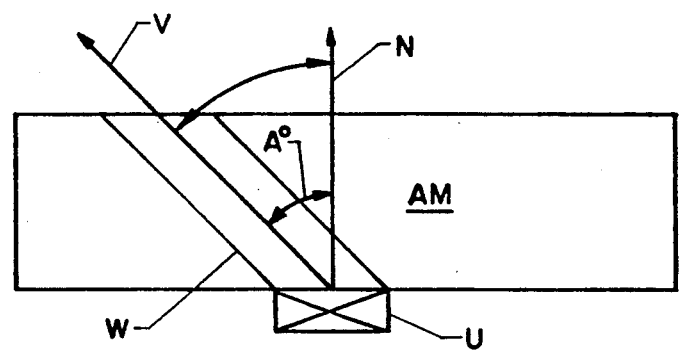
FIG. 1 is a prior art device used to show the energy flux deviation which is dependent on the elastic coefficients of the material.
Figure 2:
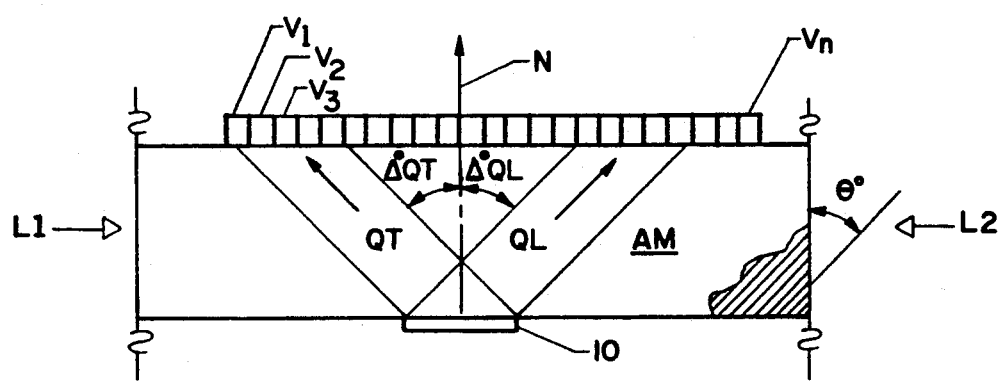
FIG. 2 is an apparatus according to the present invention for determining loads in anisotropic non-crystalline materials using energy flux deviation.

Referring to FIG. 2, a transmitting ultrasonic transducer 10 is acoustically coupled to a non-crystalline, highly anisotropic material AM, e.g., a graphite fiber-reinforced composite such as graphite/epoxy, graphite/magnesium or graphite/aluminum. The ultrasonic transducer 10 propagates an ultrasonic wave through the anisotropic material AM which initially has a wave front which is normal to directional arrow N. As discussed in greater detail below, an applied load L1 and L2 causes energy flux deviation angles of $\Delta°QL$ and $\Delta°QT$. These propagation directions change with the respective applied loads. The directional arrows QL and QT are normal to the deflected wave fronts.

The following variables are used throughout the description of the invention:

$\theta$ angle, measured from the normal vector N, of fiber orientation of anisotropic material AM;

QT vector designating "quasi-transverse" particle displacement of the propagated ultrasonic wave;

QL vector designating "quasi-longitudinal" particle displacement of the propagated ultrasonic wave;

$\Delta°QT$ angle, measured from the normal vector N, of energy flux deviation in QT direction; and $\Delta°QL$ angle, measured from the normal vector N, of energy flux deviation in QL direction.

An array of receiving transducers respectively labeled $V_1, V_2, V_3, \ldots V_N$ are acoustically coupled to the non-crystalline, highly anisotropic material AM opposite transmitting transducer 10. The receiving transducers are arranged such that adjacent transducers can detect the desired increment of propagation shift, i.e., of the deviation of energy flux, of the wave. Such an array is disclosed in U.S. Pat. No. 4,499,770, the specification of which is hereby incorporated by reference. The transmitting and receiving transducers can be any conventional type such as piezoelectric or capacitive sensors. The receiver can alternatively be a scanned optical ultrasonic receiver or any array of such receivers.

Figure 3:
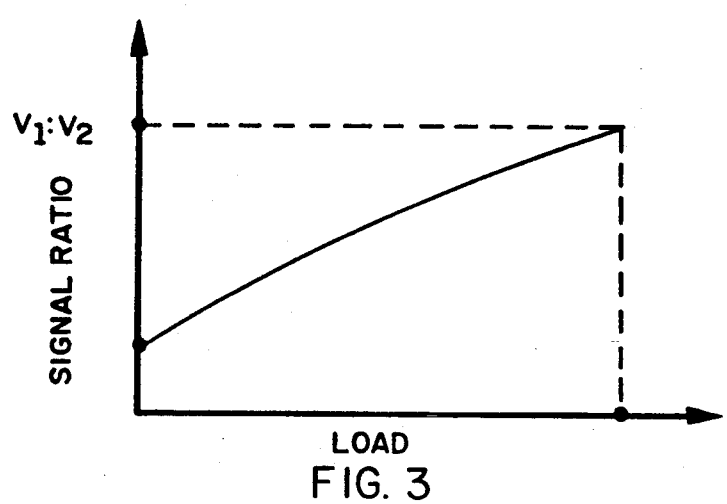
FIG. 3 is a representative graph correlating the signal ratio of two adjacent receiving transducers and the applied load.

As known, the received ultrasonic wave is converted by each receiving transducer into a respective electrical signal having a voltage proportional to the wave intensity. In one embodiment, the shift in propagation caused by an applied load is monitored as a simple ratio between two adjacent receiving transducers, e.g., $V_2:V_3$. A sample correlation between the applied load and this signal ratio is shown in FIG. 3. Material specific data curves are used to determine the applied load on that material with the measured signal ratio.

In a more specific application, the effects of nonlinear elasticity on energy flux deviation in unidirectional composites such as graphite/epoxy (gr/ep) was considered. The angle of the energy flux deviation, $\Delta QT$ or $\Delta QL$, for such a material was shown to be a function of applied stress as a result of this elastic nonlinearity. This deviation was modeled as detailed below using acousto-elastic theory and second and third order elastic stiffness coefficients for T300/5208 gr/ep previously determined in NASA Contractor Report 4100, "Ultrasonic Characterization of the Nonlinear Elastic Properties of Undirectional Graphite/Epoxy Composites", William H. Prosser, Oct., 1987.

Assuming linear elasticity, the components of the energy flux vector ($E_j$) are a function of the linear elastic stiffness coefficients $C_{ijkl}$ and the spatial and time derivatives of the displacement vector ($u_j$). The equation is given by $$E_j = -C_{ijkl}\left(\frac{\partial u_k}{\partial x_1}\right)\left(\frac{\partial u_i}{\partial t}\right) \quad (1)$$

where the Einstein summation convention on repeated indices is assumed throughout this discussion. The angle of energy flux deviation can then be calculated as the angle between the flux vector and the normal to the plane wave front.

To include non-linear elastic effects on the energy flux deviation, acoustoelastic theory is used. This theory predicts an "effective" linear elastic stiffness tensor ($c^*_{ijkl}$) that is a function of the second and third order elastic coefficients and the applied stress ($\sigma_{ij}$), as described in a communication to applicants from Dr. David M. Barnett of Stanford University. The expression for the "effective" stiffness tensor is given by $$c^*_{nlij} = k_{nlij} + \sigma_{nj}\delta_{li} \quad (2)$$

where $\delta_{li}$ is the Kronecker delta and $k_{nlij}$ is given by $$k_{nlij} = C_{nlij} + C_{rlij}\epsilon_{nr} + C_{nsij}\epsilon_{is} + C_{nlpj}\epsilon_{ip} + C_{nliq}\epsilon_{jq} + \\ C_{nlijuv}\epsilon_{uv} + C_{rlijuv}\epsilon_{uv}\epsilon_{nr} + C_{nsijuv}\epsilon_{uv}\epsilon_{is} + \\ C_{nipjuv}\epsilon_{uv}\epsilon_{ip} + C_{nliquv}\epsilon_{uv}\epsilon_{jq}. \quad (3)$$

In this expression, $c_{ijkluv}$ are the third order elastic stiffness coefficients and $\epsilon_{ij}$ are the strains resulting from the applied stresses. If the applied stresses are within the linear elastic regime, the strains are given by $$\epsilon_{ij} = s_{ijkl}\sigma_{kl} \quad (4)$$

where $s_{ijkl}$ are the linear elastic compliances which are the inverse of the stiffnesses.

Thus, if the linear elastic stiffnesses and compliances, the third order elastic stiffnesses, and the applied stresses are known, an "effective" stiffness tensor can be calculated. This can then be used to compute the changes in energy flux deviation as a function of applied stress which are a result of nonlinear elastic effects.

The effect of stress on the energy flux deviation was modeled for unidirectional T300/5208 gr/ep which was assumed to be transversely isotropic. The fiber axis was designated to be the $x_3$ axis while the laminate stacking direction which is perpendicular to the fibers was chosen to be the $x_1$ axis. The values of the previously measured non-zero independent linear elastic stiffness and compliance coefficients for this material are listed in Table 1. Likewise, the values of the previously measured non-independent non-zero third order stiffness coefficient are given in Table 2. In both tables, the contracted subscript matrix notation is used.

TABLE 1

| Linear Elastic Stiffness and Compliance Coefficients | | | |
|---|---|---|---|
| $C_{ij}$ | (GPa) | $S_{ij}$ | $(GPa)^{-1}$ |
| $C_{11}$ | 14.26 | $S_{11}$ | 0.092 |
| $C_{12}$ | 6.78 | $S_{12}$ | $-0.042$ |
| $C_{13}$ | 6.5 | $S_{13}$ | $-0.003$ |
| $C_{33}$ | 108.4 | $S_{33}$ | 0.0096 |
| $C_{44}$ | 5.27 | $S_{44}$ | 0.190 |

TABLE 2

| Third Order (Non-Linear) Elastic Stiffness Coefficients | | | |
|---|---|---|---|
| $C_{ijk}$ | (GPa) | $C_{ijk}$ | (GPa) |
| $C_{111}$ | $-196$ | $C_{155}$ | $-49.1$ |
| $C_{112}$ | $-89$ | $C_{344}$ | $-47$ |
| $C_{113}$ | $-4$ | $C_{133}$ | $-236$ |
| $C_{123}$ | 65 | $C_{333}$ | $-829$ |
| $C_{144}$ | $-33.4$ | | |

Calculations were performed for elastic waves propagating in the $x_1x_3$ plane. As in any anisotropic bulk material, three elastic waves will propagate along any direction in this plane. Of the three waves propagating in this plane, one of them is always a pure mode transverse (PT) wave with its particle displacement polarized perpendicular to the $x_1$ and $x_3$ axes, i.e., along the $x_2$ axis. The other two modes are quasi-mode waves with components of particle displacements both along their direction of propagation and perpendicular to it. One is a quasi-transverse (QT) mode wave while the other is a quasi-longitudinal (QL) mode wave. All three modes suffer energy flux deviation except for propagation along the fiber axis ($x_3$) and the laminate stacking axis ($x_1$). These are symmetry directions along which all three modes are pure mode waves and none suffers energy flux deviation.

Figure 5:
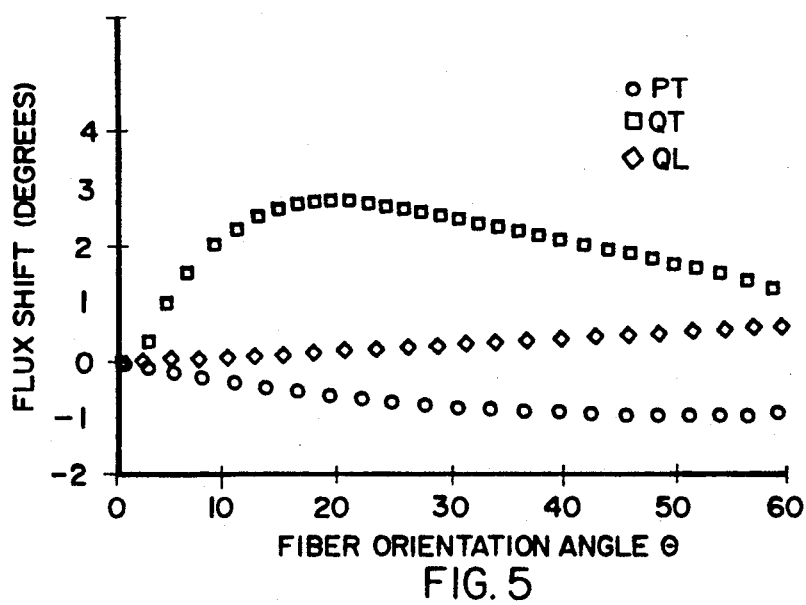
FIG. 5 is a graph of the shift in energy flux deviation as a function of the fiber orientation angle due to a 1 GPa load applied along the $x_3$ axis, i.e., in the fiber direction.
Figure 6:
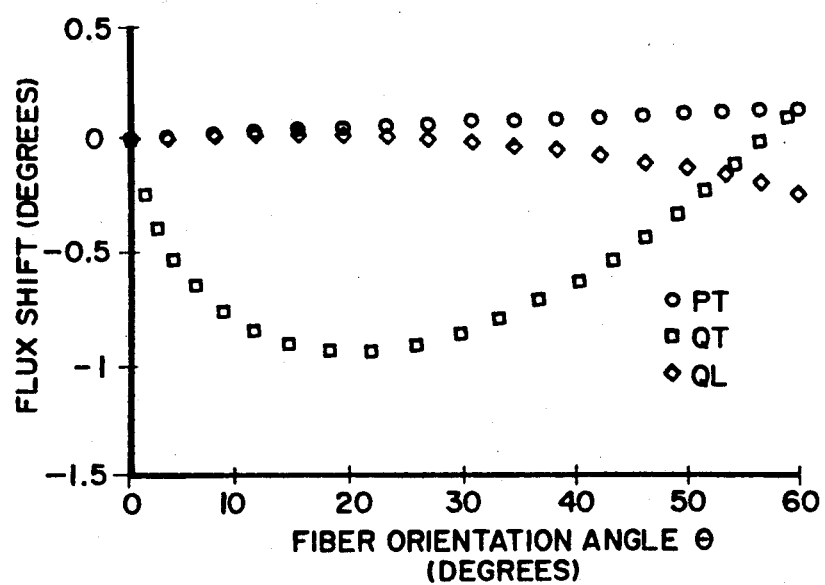
FIG. 6 is a graph of the shift in energy flux deviation as a function of the fiber orientation angle due to a 0.1 GPa load applied along the $x_1$ axis, i.e., in the laminate stacking direction.

The energy flux deviation was first computed for the condition of no applied stress. Then, calculations were performed for two different states of uniaxial stress. The first was stress along the fiber direction ($x_3$) of a magnitude of 1 GPa, as shown in FIG. 5. The second was along the laminate stacking ($x_1$) direction with a magnitude of 0.1 GPa, as shown in FIG. 6. These values are near the reported ultimate strengths of this material along the respective directions. This allows an estimate of the maximum effects of stress on energy flux deviation. For both conditions, the change in the energy flux deviation angle from the condition of zero applied stress was computed over the range of propagation directions of 0° to 60° from the fiber axis at 2° intervals.

Figure 4:
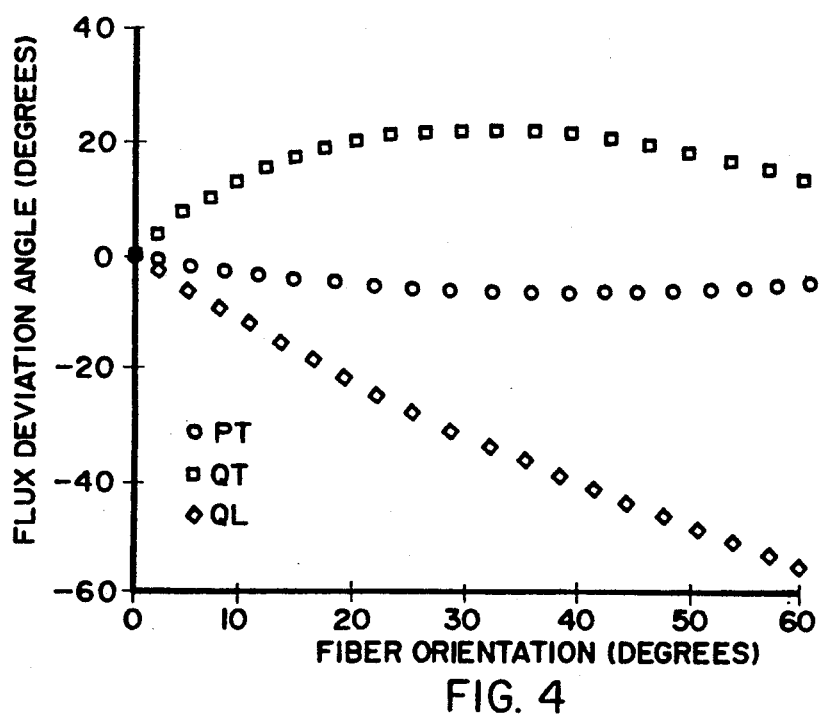
FIG. 4 is a graph of the energy flux deviation as a function of the fiber orientation angle in a no applied stress condition.

The flux deviation angles of the three modes as a function of fiber orientation at zero stress are plotted in FIG. 4. The fiber orientation angle is the angle between the fibers and the normal N to the wave front or the intended direction of propagation. A positive flux deviation angle implies the energy deviates away from the fiber direction toward the $x_1$ axis while a negative deviation means that the energy deviates toward the fibers. Over this range of fiber orientation angles, the energy of the QL and PT mode waves deviates toward the fibers while that of the QT deviates away from the fibers.

In FIG. 5, the change in the predicted energy flux deviation due to the application of stress along the fibers is plotted as a function of fiber orientation angle. The energy of the QT mode wave suffers the largest shift in flux deviation, reaching a maximum of 3° at a propagation direction of approximately 20° with respect to the fiber direction. The energy of the PT mode wave changes by a smaller amount in the opposite direction while the QL mode wave suffers a negligible shift.

The relative magnitudes of the flux deviation shifts of the different modes can be explained qualitatively by considering the ratios of the magnitude of the non-linear elastic coefficients to the linear coefficients. The primary elastic coefficients affecting the propagation of the PT and QL modes are those dominated by the matrix properties. These coefficients are $c_{11}$, $c_{12}$, $c_{44}$, $c_{111}$, and $c_{112}$. The magnitude of the non-linear coefficients are over an order of magnitude larger than the linear coefficients in this case. However, the ratios of the non-linear to linear coefficients which dominate the QL wave ($c_{33}$, $c_{133}$, and $c_{333}$) are much smaller even though the magnitudes of the individual coefficients are larger. Therefore, the effect of non-linear elasticity on the energy flux deviation should be much smaller for the QL mode wave. The previous measurements of the effect of matrix degradation on energy flux deviation also showed a larger change in the flux deviation of the QT mode wave with almost no change in the QL mode wave.

The shift in energy flux deviation due to applied stress along the $x_1$ axis is shown in FIG. 6. Again the QT mode wave suffers the largest change in flux deviation angle while the QL mode is almost unchanged. It is interesting to note that the direction of the change in energy flux is in the opposite direction from the case of applied stress along the fiber direction.

These calculations demonstrate the effect of nonlinear elasticity on the energy flux deviation of ultrasonic waves in gr/ep composite materials. The modes indicate the angles of fiber orientation and wave modes that suffer the maximum shift in flux deviation for the cases of applied stress considered. Although the models presented were for bulk waves propagating through a thick composite material, the same effect is expected for plane plate waves propagating in thin plates. The longer propagation paths possible along plates would make the effect more measurable and thus could improve the stress resolution. This effect is used to develop a new nondestructive method for monitoring stress in composite materials or as a new method for measuring their nonlinearity.

In practice, data for flux shifts are generated for a specific material having a specific fiber orientation at known loads. A family of curves for different loads could be generated with each curve representing a different load condition as shown by way of example in FIGS. 5 and 6 where only one load condition is depicted. This data and a subsequently determined flux shift allows one to approximate the value of an unknown load which caused this flux shift.

Specifically, an ultrasonic wave is applied to a particular anisotropic sample material in an initial direction and an angle of flux deviation of the ultrasonic wave front measured from this initial direction. As discussed previously, this flux deviation angle is induced by the unknown applied load. Next, the flux shift is determined between this flux deviation angle and a previously determined angle of flux deviation of an ultrasonic wave applied to a similar, or the particular, anisotropic reference material under an initial known load condition such as a no load condition. This determined flux shift is compared to a plurality of flux shifts of a similarly tested, similar anisotropic reference material, or the particular sample material, under a plurality of respective, known load conditions, whereby the load applied to a particular anisotropic sample material is determined. The "similar" anisotropic material(s) are similar in that they possess similar fiber orientation, i.e., they exhibit flux shifts similar to those of the particular anisotropic sample material.

The unknown quantity could likewise be fiber orientation of a known material, wherein a determined flux shift caused by a known load allows for approximation of the fiber orientation, as shown in FIGS. 5 and 6. An ultrasonic wave is first applied in an initial direction to a particular anisotropic sample material under a known load and having unknown fiber orientation. Next, an angle of flux deviation of the ultrasonic wave front from the initial direction is measured. A flux shift is then determined between this measured flux deviation angle and a previously determined angle of flux deviation of an ultrasonic wave applied to the particular anisotropic sample material under a known load such as a no load condition. This flux shift is then compared to a plurality of flux shifts of a plurality of anisotropic reference materials having a plurality of respectively known fiber orientations and similarly tested under the same load conditions as the particular material, whereby the fiber orientation of the particular anisotropic material sample is determined. These reference materials are "similar" in that they are the same composite as the particular sample but have various fiber orientations.

Many modifications, improvements and substitutions will be apparent to the skilled artisan without departing from the spirit and scope of the present invention as described in the application and defined in the following claims.

What is claimed is:

1. A method of determining an applied load of a particular anisotropic sample material comprising the steps of:
    applying an ultrasonic wave to the particular anisotropic sample material in an initial direction;
    measuring an angle of flux deviation of the ultrasonic wave front from the initial direction, the flux deviation angle induced by the applied load;
    determining a flux shift between this load-induced flux deviation angle and a previously determined angle of flux deviation of an ultrasonic wave applied to a similar anisotropic reference material under an initial known load condition; and
    comparing this said flux shift to a plurality of previously determined flux shifts of a similarly tested, similar anisotropic reference material tested under a plurality of respective known load conditions, whereby the load applied to the particular anisotropic sample material is determined by correlating said flux shifts to previously determined flux shifts due to known loads in said reference material.

2. The method according to claim 1, wherein said measuring step comprises measuring the angle of flux deviation in a quasi-transverse wave direction, wherein said quasi-transverse wave direction is the direction in which particle motion of the wave is predominantly perpendicular to the direction of wave propagation.

3. The method according to claim 1, wherein said measuring step comprises measuring the angle of flux deviation in a quasi-longitudinal direction, wherein said quasi-longitudinal wave direction is the direction in which particle motion of the wave is predominantly parallel to the direction of wave propagation.

4. The method according to claim 1, wherein the particular anisotropic material is non-crystalline.

5. The method according to claim 4, wherein the non-crystalline, anisotropic material is a graphite fiber-reinforced composite.

6. The method according to claim 5, wherein said measuring step comprises measuring the angle of flux deviation in a quasi-transverse wave direction, wherein said quasi-transverse wave direction is the direction in which particle motion of the wave is predominantly perpendicular to the direction of wave propagation.

7. The method according to claim 5, wherein said measuring step comprises measuring the angle of flux deviation in a quasi-longitudinal direction, wherein said quasi-longitudinal wave direction is the direction in which particle motion of the wave is predominantly parallel to the direction of wave propagation.

8. The method according to claim 5, wherein the graphite fiber-reinforced composite material is selected from a group consisting of graphite/epoxy, graphite/magnesium and graphite/aluminum.

9. The method according to claim 8, wherein said measuring step comprises measuring the angle of flux deviation in a quasi-transverse wave direction, wherein said quasi-transverse wave direction is the direction in which particle motion of the wave is predominantly perpendicular to the direction of wave propagation.

10. The method according to claim 8, wherein said measuring step comprises measuring the angle of flux deviation in a quasi-longitudinal direction, wherein said quasi-longitudinal wave direction is the direction in which particle motion of the wave is predominantly parallel to the direction of wave propagation.

11. The method according to claim 1, wherein the initial known load condition is a no-load condition.

12. The method according to claim 1, wherein said applying step comprises disposing a means for transmitting an ultrasonic wave on a surface of the anisotropic material and said measuring step comprises arranging means for receiving the transmitted ultrasonic wave on another surface of the anisotropic material opposite said means for transmitting an ultrasonic wave.

13. The method according to claim 12, wherein the transmitting means is an ultrasonic transducer.

14. The method according to claim 12, wherein the receiving means is an array of receiving transducers.

* * * * *